US010989806B2

(12) United States Patent
Campbell et al.

(10) Patent No.: US 10,989,806 B2
(45) Date of Patent: Apr. 27, 2021

(54) HOME OCCUPANT DETECTION AND MONITORING SYSTEM

(71) Applicant: PRAESIDIUM, INC., Washington, UT (US)

(72) Inventors: Seth Campbell, Washington, UT (US); Richard Curtis Nordgran, Springville, UT (US); Weston Brent Johnson, St. George, UT (US); Paolo Focardi, Pasadena, CA (US); Gian Franco Sacco, Pasadena, CA (US); Jim Butler, Sierra Madre, CA (US)

(73) Assignee: PRAESIDIUM, INC., Washington, UT (US)

( * ) Notice: Subject to any disclaimer, the term of this patent is extended or adjusted under 35 U.S.C. 154(b) by 365 days.

(21) Appl. No.: 15/916,215

(22) Filed: Mar. 8, 2018

(65) Prior Publication Data

US 2018/0259638 A1    Sep. 13, 2018

Related U.S. Application Data

(60) Provisional application No. 62/468,805, filed on Mar. 8, 2017, provisional application No. 62/520,258, filed on Jun. 15, 2017.

(51) Int. Cl.
*G01S 13/88* (2006.01)
*G01S 7/00* (2006.01)
(Continued)

(52) U.S. Cl.
CPC ............ *G01S 13/886* (2013.01); *A61B 5/002* (2013.01); *A61B 5/02444* (2013.01);
(Continued)

(58) Field of Classification Search
CPC combination set(s) only.
See application file for complete search history.

(56) References Cited

U.S. PATENT DOCUMENTS 3,524,058 A    8/1970    Robertson et al.
3,796,208 A    3/1974    Bloice
(Continued)

FOREIGN PATENT DOCUMENTS

CN    103021118 A    4/2013
CN    205068696 U    3/2016
(Continued)

OTHER PUBLICATIONS

International Search Report and Written Opinion of the International Searching Authority for PCT Application No. PCT/US2017/47870 (dated Dec. 26, 2017).
(Continued)

*Primary Examiner* — Mamadou L Diallo
(74) *Attorney, Agent, or Firm* — Gurr Brande & Spendlove, PLLC.; Robert Spendlove (57) ABSTRACT

A home occupant detection and monitoring system has a sensor unit having a radio wave transmitter, a radio wave receiver, and a wireless transmitter configured to detect and receive vital signs of an occupant; a user interface having a microcontroller, a wireless receiver configured to receive the wireless signals transmitted from the sensor unit, a means for user input, and a network card; and a means for alerting occupants and third-parties to a triggering event; wherein the microcontroller, based upon logic, activates the alerting means at the triggering event.

20 Claims, 6 Drawing Sheets

(51) Int. Cl.

| | | |
|---|---|---|
| *G01S 7/35* | (2006.01) | |
| *G01S 13/04* | (2006.01) | |
| *G01S 13/34* | (2006.01) | |
| *G01S 7/41* | (2006.01) | |
| *A61B 5/08* | (2006.01) | |
| *G08B 13/187* | (2006.01) | |
| *A61B 5/00* | (2006.01) | |
| *A61B 5/0507* | (2021.01) | |
| *G08B 21/04* | (2006.01) | |
| *A61B 5/11* | (2006.01) | |
| *A61B 5/1495* | (2006.01) | |
| *A61B 5/024* | (2006.01) | |

(52) U.S. Cl.
CPC .......... *A61B 5/0507* (2013.01); *A61B 5/0816* (2013.01); *A61B 5/1113* (2013.01); *A61B 5/1495* (2013.01); *A61B 5/4088* (2013.01); *A61B 5/7465* (2013.01); *G01S 7/003* (2013.01); *G01S 7/35* (2013.01); *G01S 7/412* (2013.01); *G01S 7/415* (2013.01); *G01S 13/04* (2013.01); *G01S 13/34* (2013.01); *G08B 13/187* (2013.01); *G08B 21/0469* (2013.01); *A61B 5/7267* (2013.01); *A61B 2562/04* (2013.01); *G01S 7/414* (2013.01)

(56) References Cited

U.S. PATENT DOCUMENTS

| | | |
|---|---|---|
| 3,875,929 A | 4/1975 | Grant |
| 3,993,995 A | 11/1976 | Kaplan et al. |
| 4,085,740 A | 4/1978 | Allen, Jr. |
| 4,197,856 A | 4/1980 | Northrop |
| 4,289,142 A | 9/1981 | Kearns |
| 4,958,638 A | 9/1990 | Sharpe et al. |
| 5,107,845 A | 4/1992 | Guern et al. |
| 6,062,216 A | 5/2000 | Corn |
| 6,150,941 A | 11/2000 | Geiger et al. |
| 6,359,597 B2 | 3/2002 | Haj-Yousef |
| 6,483,929 B1 | 11/2002 | Murakami et al. |
| 6,583,730 B2 | 6/2003 | Lang et al. |
| 6,693,535 B2 | 2/2004 | Van Bosch et al. |
| 6,753,780 B2 | 6/2004 | Li |
| 6,922,147 B1 | 7/2005 | Viksnins et al. |
| 6,922,622 B2 | 7/2005 | Dulin et al. |
| 7,036,390 B2 | 5/2006 | Tsuchihashi et al. |
| 7,348,880 B2 | 3/2008 | Hules et al. |
| 7,536,557 B2 | 5/2009 | Murakami et al. |
| 7,903,020 B2 | 3/2011 | Lin et al. |
| 7,948,361 B2 | 5/2011 | Bennett et al. |
| 8,031,912 B2 | 10/2011 | Dennis et al. |
| 8,044,782 B2 | 10/2011 | Saban |
| 8,232,874 B1 | 7/2012 | Aneiros et al. |
| 8,428,696 B2 | 4/2013 | Foo |
| 8,494,615 B2 | 7/2013 | Melamed et al. |
| 8,562,526 B2 | 10/2013 | Heneghan et al. |
| 8,611,954 B2 | 12/2013 | Gross |
| 8,740,793 B2 | 6/2014 | Cuddihy et al. |
| 8,922,342 B1 | 12/2014 | Ashenfelter et al. |
| 8,932,217 B2 | 1/2015 | Gibson et al. |
| 9,000,907 B1 | 4/2015 | Rembach et al. |
| 9,184,773 B2 | 11/2015 | Nadiri et al. |
| 9,195,799 B2 | 11/2015 | Sze et al. |
| 9,227,484 B1 | 1/2016 | Justice et al. |
| 9,244,021 B2 | 1/2016 | Melamed |
| 9,530,080 B2 | 12/2016 | Glazer |
| 9,547,070 B2 | 1/2017 | Corcos et al. |
| 9,552,469 B2 | 1/2017 | Jin et al. |
| 9,553,621 B2 | 1/2017 | Nadiri et al. |
| 9,577,992 B2 | 2/2017 | Zizi et al. |
| 9,589,106 B2 | 3/2017 | Bangera et al. |
| 9,590,986 B2 | 3/2017 | Zizi et al. |
| 9,595,143 B1 | 3/2017 | Ashenfelter et al. |
| 9,615,765 B2 | 4/2017 | Chayat |
| 9,625,508 B2 | 4/2017 | Chayat |
| 9,735,899 B2 | 8/2017 | Moshe |
| 9,813,281 B2 | 11/2017 | Nadiri et al. |
| 9,853,976 B2 | 12/2017 | Zizi et al. |
| 9,869,707 B2 | 1/2018 | Cohen |
| 9,876,590 B2 | 1/2018 | Lomnitz |
| 9,964,505 B2 | 5/2018 | Melamed |
| 10,020,836 B2 | 7/2018 | Chayat et al. |
| 10,041,986 B2 | 8/2018 | Nadiri et al. |
| 10,054,096 B2 | 8/2018 | Berkson |
| 10,056,186 B2 | 8/2018 | Rosenfeld |
| 10,061,911 B2 | 8/2018 | Zizi et al. |
| 10,153,531 B2 | 12/2018 | Chayat |
| 10,154,422 B2 | 12/2018 | Chayat |
| 10,182,738 B2 | 1/2019 | Melamed |
| 10,401,490 B2* | 9/2019 | Gillian ............... G06F 21/6245 |
| 10,813,809 B2 | 10/2020 | Sauser et al. |
| 10,912,693 B2 | 2/2021 | Baker et al. |
| 2002/0057202 A1 | 5/2002 | Luzon |
| 2003/0098784 A1 | 5/2003 | Bosch et al. |
| 2003/0201894 A1* | 10/2003 | Li ........................ B60N 2/002 340/573.1 |
| 2004/0020314 A1 | 2/2004 | Tsuchihashi et al. |
| 2004/0056954 A1 | 3/2004 | Crandall et al. |
| 2005/0024188 A1 | 2/2005 | Sider |
| 2006/0025897 A1* | 2/2006 | Shostak ................ G08G 1/017 701/1 |
| 2007/0013531 A1 | 1/2007 | Hules et al. |
| 2009/0203972 A1 | 8/2009 | Heneghan et al. |
| 2009/0227882 A1 | 9/2009 | Foo |
| 2010/0241018 A1 | 9/2010 | Vogel |
| 2012/0059268 A1 | 3/2012 | Tupin, Jr. |
| 2012/0203078 A1 | 8/2012 | Sze et al. |
| 2013/0001422 A1 | 1/2013 | Lavon et al. |
| 2013/0065641 A1 | 3/2013 | Gross |
| 2013/0173926 A1 | 7/2013 | Morese et al. |
| 2013/0201013 A1 | 8/2013 | Schoenberg |
| 2014/0089007 A1* | 3/2014 | Sim ........................ G16H 10/60 705/3 |
| 2014/0159912 A1 | 6/2014 | Fraden |
| 2014/0207282 A1* | 7/2014 | Angle ................ H04L 12/2809 700/257 |
| 2014/0266704 A1* | 9/2014 | Dalley, Jr. .............. G08B 21/18 340/539.13 |
| 2014/0276031 A1 | 9/2014 | Lomnitz et al. |
| 2015/0170503 A1* | 6/2015 | Wedig ...................... G08B 7/06 340/691.5 |
| 2015/0185314 A1 | 7/2015 | Corcos et al. |
| 2015/0266395 A1 | 9/2015 | Bradley et al. |
| 2015/0274036 A1 | 10/2015 | Arad et al. |
| 2015/0287296 A1* | 10/2015 | Hall ........................ G06K 9/00 340/541 |
| 2015/0288877 A1 | 10/2015 | Glazer |
| 2015/0311591 A1 | 10/2015 | Golombek |
| 2016/0090958 A1 | 3/2016 | Berkson |
| 2016/0167479 A1 | 6/2016 | Morin |
| 2016/0232778 A1* | 8/2016 | Honjo ................... H04W 12/08 |
| 2016/0313259 A1 | 10/2016 | Shayovitz |
| 2016/0356877 A1 | 12/2016 | Melamed et al. |
| 2017/0013069 A1* | 1/2017 | Grohman ............ H04L 12/4625 |
| 2017/0033469 A1 | 2/2017 | Hoffman et al. |
| 2017/0033808 A1 | 2/2017 | Lomnitz et al. |
| 2017/0068863 A1* | 3/2017 | Rattner ............ G06K 9/00838 |
| 2017/0153324 A1 | 6/2017 | Lomnitz |
| 2017/0184647 A1 | 6/2017 | Chayat |
| 2017/0238835 A1 | 8/2017 | Melamed |
| 2018/0000408 A1 | 1/2018 | Heinrich et al. |
| 2018/0029591 A1* | 2/2018 | Lavoie ................... G06N 7/005 |
| 2018/0050575 A1* | 2/2018 | Campbell ......... B60R 21/01536 |
| 2018/0053392 A1 | 2/2018 | White et al. |
| 2018/0053393 A1 | 2/2018 | White et al. |
| 2018/0089975 A1 | 3/2018 | Amir et al. |
| 2018/0225956 A1* | 8/2018 | Chen ............... G08B 13/19619 |
| 2018/0235542 A1* | 8/2018 | Yun ..................... A61B 5/0205 |
| 2019/0024350 A1* | 1/2019 | Silverstein ............ E03C 1/0408 |
| 2019/0049570 A1* | 2/2019 | Xiong ................... G01S 13/886 |
| 2019/0066464 A1* | 2/2019 | Wedig ................... H04W 4/024 |

(56) References Cited

U.S. PATENT DOCUMENTS

2019/0254544 A1\* 8/2019 Chayat ................. A61B 5/0022
2020/0233079 A1\* 7/2020 Silverstein .............. G01S 13/52
2021/0007921 A1 1/2021 Sauser et al.

FOREIGN PATENT DOCUMENTS

| JP | 2013108639 A | 6/2013 |
|---|---|---|
| WO | 2009083017 A1 | 7/2009 |
| WO | 2013155661 A1 | 10/2013 |
| WO | 2018035540 A1 | 2/2018 |

OTHER PUBLICATIONS

International Search Report and Written Opinion of the International Searching Authority for PCT Application No. PCT/US2018/021629 (dated Jun. 27, 2018).

International Search Report and Written Opinion of the International Searching Authority for PCT Application No. PCT/US2018/064273 (dated Feb. 14, 2019).

\* cited by examiner

HOME OCCUPANT DETECTION AND MONITORING SYSTEM

CROSS-REFERENCE TO RELATED APPLICATIONS

This application claims the benefit of U.S. Provisional Application Ser. No. 62/468,805 filed on Mar. 8, 2017, and U.S. Provisional Application Ser. No. 62/520,258 filed on Jun. 15, 2017, both of which are incorporated herein by reference.

TECHNICAL FIELD

The present disclosure relates to home security systems. More particularly, the present disclosure is directed to a system for detecting, identifying, and monitoring individuals in a home by using their heartbeat, respiration, or other vital signals.

BACKGROUND

Modern home and commercial security systems are generally comprised of three primary detection methods to detect intruders: door/window sensors, motion sensors, and glass break sensors. While these technologies can be effective in some situations, they are all possible to defeat so as to miss an intruder or unwanted occupant. As an example, glass break sensors can be defeated by a glass cutter or by simply breaking a window with minimal sound; motion sensors can be defeated by crawling or otherwise keeping a low profile while moving close to walls; and door/window sensors can be overcome with the use of magnets. Other means and methods may be available to defeat these technologies. In addition to these problems, intruders can gain access to a home or business when an alarm is not activated, lying in wait until other occupants have gone to sleep or left the business. In addition, such systems require time money and time in installing and maintaining a sensor at each door, window or other potential entry point.

Therefore, there is a need for a security system that is not limited to monitoring entry points, and that can constantly monitor occupants in a home, business, or other structure to prevent an unwanted occupant from entering, or remaining, in a structure.

Further, there are currently no systems for simultaneously monitoring the health status of each occupant within a structure. In other words, many deaths occur each year that may have been preventable, had other occupants in the home been alerted to a health emergency. For example, several children die each year from suffocation. If someone would have been alerted to the child's distress, the child might have been saved. As such, there is a need for a system that not only monitors a home for intrusion purposes, but that monitors the occupants' health statuses as well.

SUMMARY OF EXAMPLE EMBODIMENTS

In one embodiment, a home occupant detection and monitoring system comprises a sensor unit comprising a radio wave transmitter, a radio wave receiver, and a wireless transmitter; a user interface comprising a microcontroller, a wireless receiver configured to receive the wireless signals transmitted from the sensor unit, a means for user input, and a network card; and, a means for alerting occupants and third-parties to a triggering event; wherein the microcontroller, based upon logic, activates the alerting means at a triggering event.

In one embodiment, a home occupant detection and monitoring system further comprises one or more cameras aligned with the sensor unit, the camera configured to activate and/or record at a triggering event.

In one embodiment, a home occupant detection and monitoring system comprises a radio wave transmitter capable of transmitting Frequency Modulated Continuous Wave (FMCW) signals; one or more radio wave receivers positioned in orthogonal locations (or, in general, non-parallel locations) around an environment to be monitored; a user interface comprising a microcontroller, a wireless transceiver, a means for user input, and a network card; and, a means for alerting occupants and third-parties to a triggering event; wherein the microcontroller, based upon logic, activates the alerting means at a triggering event.

In one embodiment, a home occupant detection and monitoring system comprises a radio wave transmitter capable of transmitting FMCW, wherein the FMCW is configured to map walls of a structure by measuring distance of walls and objects with maximum return.

In one embodiment, an antenna of the radio wave transmitter, receiver, or transceiver rotates, either electronically or mechanically, to monitor an environment using narrow beam scanning (e.g., +/−45 deg.). In an alternate embodiment, the antenna would use wide (e.g., 90 deg.) beam scanning with a moveable, higher gain antenna to scan the environment for vital signals.

In one embodiment, a method of detecting occupants in a structure comprises using radar to detect one or more occupants within a structure, comparing the total number of occupants within the structure with the total number of occupants allowed in the structure as programmed by a user; and, alerting one or more individuals when the number of occupants within a structure drops below, or exceeds, a predetermined threshold.

In one embodiment, a method of detecting occupants in a structure comprises using radar to detect one or more occupants within a structure, using programmed logic to compare the radar signals with one or more stored signals, and identifying the occupants based upon the radar signals.

In one embodiment, a method of detecting, identifying, and monitoring users comprises using radar to detect one or more occupants within a structure, using programmed logic to compare the radar signals with one or more stored signals, and identifying the occupants based upon the radar signals, wherein when an irregular radar signal is received from one or more known occupants, alerting one or more occupants to the irregular radar signal received.

DETAILED DESCRIPTION OF EXAMPLE EMBODIMENTS

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiment," and the like, may indicate that the embodiment(s) so described may include a particular feature, structure, or characteristic, but not every embodiment necessarily includes the particular features, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may. Further, not all drawings may be drawn to scale.

Accordingly, the particular arrangements disclosed are meant to be illustrative only and not limiting as to the scope of the invention. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed process or methods generally may be carried out in various different sequences and arrangements while still falling within the scope of the present invention.

The term "coupled" may mean that two or more elements are in direct physical or electrical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

While the term "home" may be used throughout the disclosure, the scope of the invention is not so limited. In other words, the system disclosed herein may be used in any structure or environment. Further, as used herein, an "occupant" may refer to a person or an animal.

As will be appreciated from the below disclosure, the home occupant detection and monitoring system solves the problems in the prior art—namely, the ability to monitor more than entry/exit points, and detecting the presence of an individual without the shortcomings of motion sensors. Further, the ability to monitor various health aspects of individuals within a home is an added benefit of the system disclosed herein. Some benefits of using heartbeat and breathing detection to monitor occupants include: 1) the ability to penetrate walls and concrete using radio waves so that an intruder cannot hide from detection, which would more readily detect and deter intruders from entering a premise; 2) the ability to detect when an individual has left the premise, such as a child sneaking out at night or other similar situations; and 3) the ability to monitor the health of individuals within a home or structure and potentially prevent injury or death by alerting occupants or authorities to potential health events, such as a child choking, an infant not breathing while asleep, an occupant experiencing a stroke, cardiac event, or respiratory distress, or other health event. This system disclosed herein is programmable to the specific occupants of the home and is able to alert other occupants of the home when one of the occupants is experiencing a health issue, has left the premises, or other programmable event. It also has the ability to alert the occupants to the entry of an unknown occupant.

Figure 5:
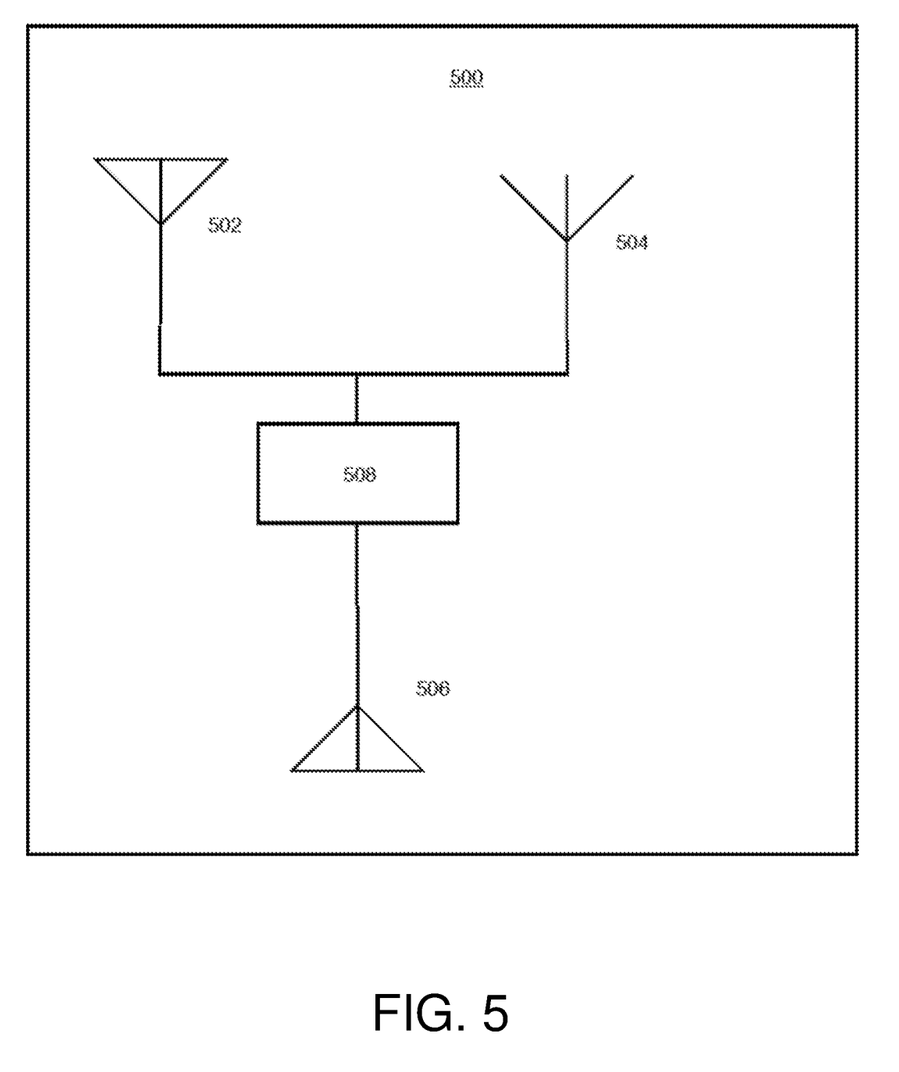
FIG. 5 is a block diagram showing components of a sensor for use with a home occupant detection and monitoring system.

In one embodiment, as illustrated by the block diagram of FIG. 5, a home occupant detection and monitoring system comprises a sensor unit 500 comprising a radio wave transmitter 502, a radio wave receiver 504, and a wireless transmitter 506. It will be appreciated that the radar components (e.g., radio wave transmitter and receiver) may comprise components known in the industry; i.e., a radar system comprises a transmitter producing electromagnetic radio waves, a transmitting antenna, a receiving antenna, and a receiver. Additionally, it will be understood that the transmitter 502 and receiver 504 may use the same antenna for transmitting and receiving. Further, the wireless transmitter may be capable of both sending and receiving signals. The sensor unit 500 may include electronic circuitry 508 as would be understood by one of ordinary skill in the art. Such circuitry 508 may include provisions for transforming, analyzing, digitizing or otherwise manipulating signals or information received by the sensor unit 500. The circuitry 508 may comprise an analog-to-digital converter, a digital-to-analog converter, memory, logic circuits or other components. The circuitry 508 may comprise individual components or one or more integrated circuit boards having one or more such components. The sensor unit(s) 500 may be placed at any number of locations, as discussed in more detail below. The transmitter 502 then transmits a radio wave signal and the receiver 504 receives the returned signal.

Figure 1:
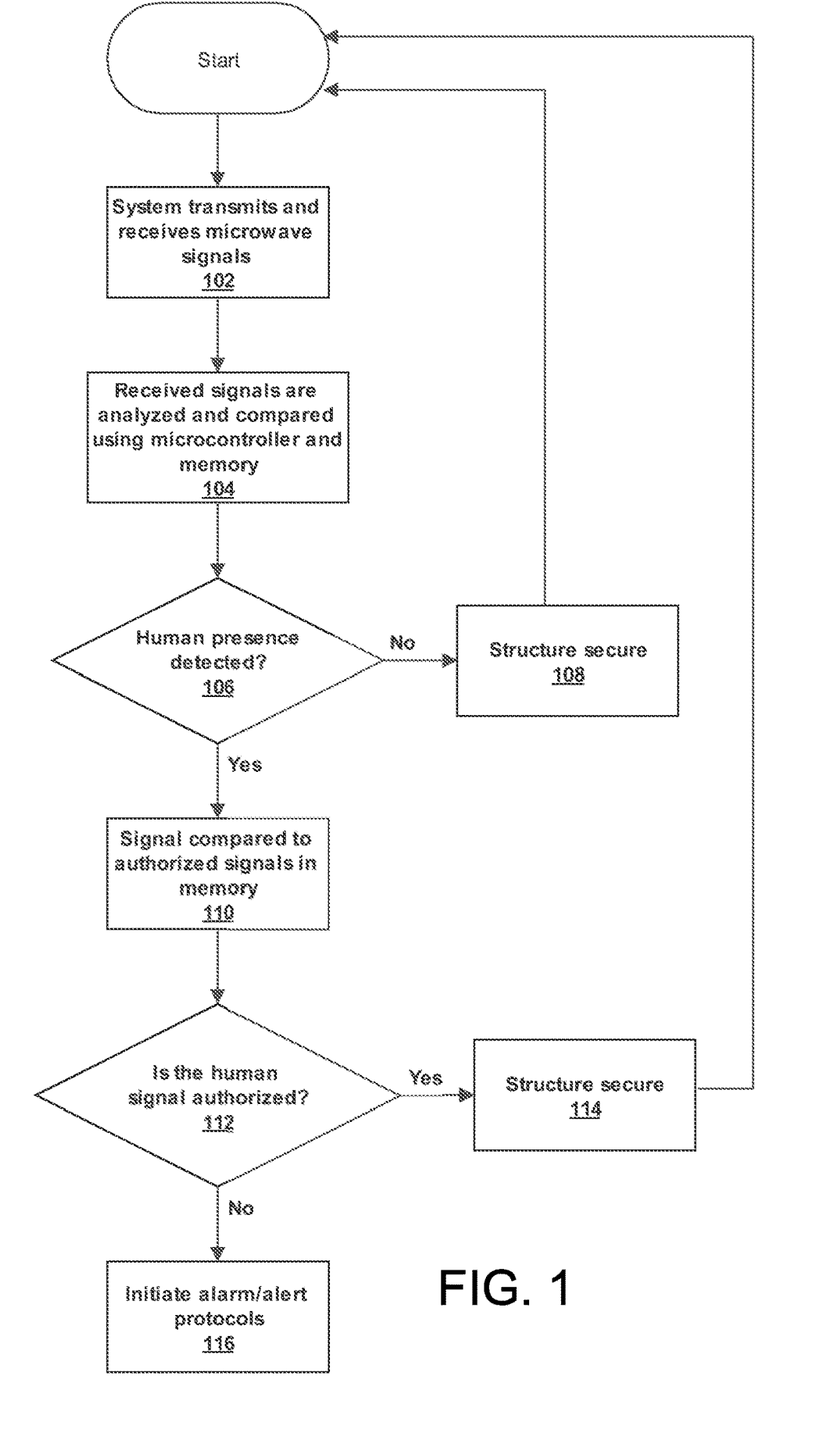
FIG. 1 is a flowchart of a home occupant detection and monitoring system.
Figure 6:
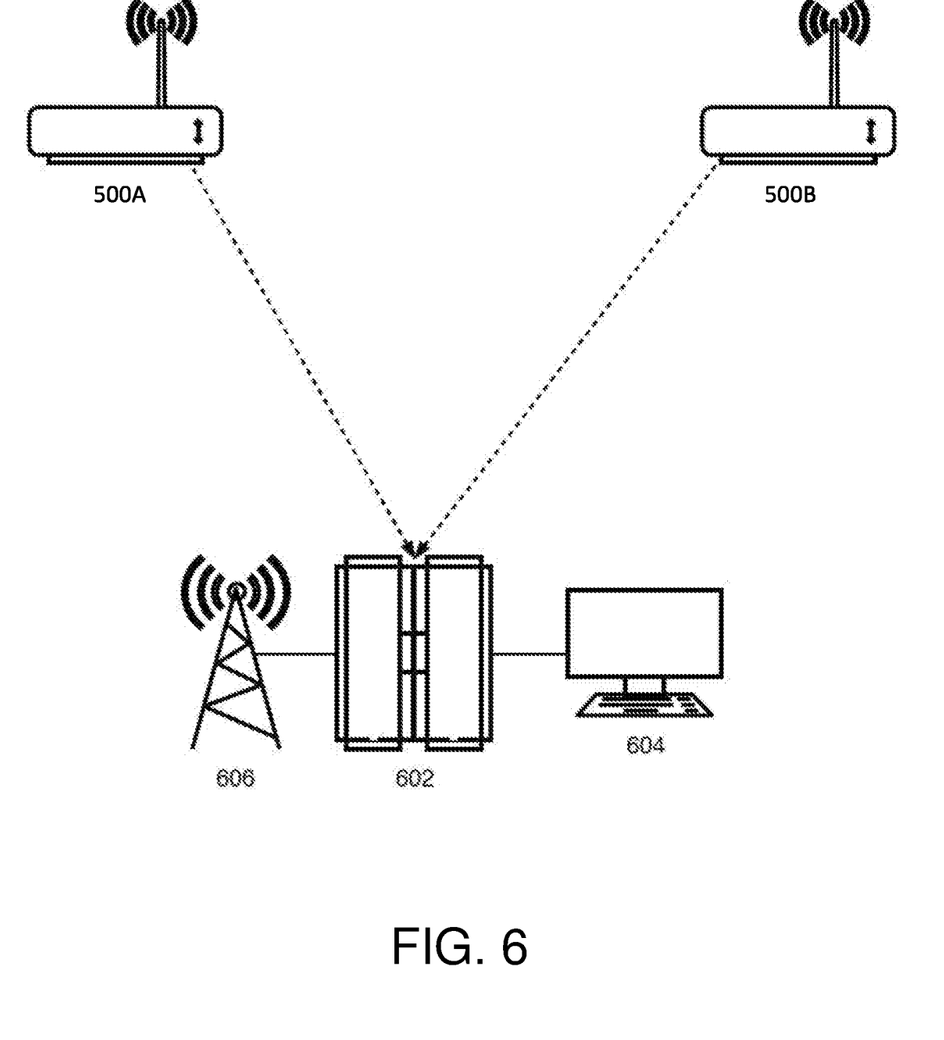
FIG. 6 is a schematic diagram of certain components of a home occupant detection and monitoring system.

As shown by the schematic diagram of FIG. 6, a monitoring system may comprise a number of elements connected into a network. The monitoring system may comprise multiple sensors 500A, 500B. While two sensors 500A, 500B are illustrated, the system may employ many more sensors distributed in a single room or in multiple rooms. As described above, the sensor transmitter 502 transmits a radio wave signal and the receiver 504 receives the returned signal. The returned signal received by the sensor 500, or a signal representative of information contained in the returned signal, is transmitted to a control unit 602 for analysis via the wireless transmitter 506. It will be appreciated that while wireless transmitters are preferred, they are not required, and wired connections may be used. Further, the network need not require the internet and may be a local area network, mesh network, or other method of communication. The control unit 602 ideally comprises a user interface, a microcontroller, a wireless receiver 606 configured to receive the wireless signals transmitted from the sensor unit 500A, 500B, a user input device, and a network communication device such as a network card (wired, wireless, or equivalent communication protocol, including, Bluetooth, ZigBee, wifi, cellular, LoRa, IR, UART, ASK, FSK and others). The user interface, microcontroller, user input device and other elements of the control unit 602 may form part of a user terminal 604. The user terminal 604 may be a personal computer, a personal electronic device such as a tablet or smartphone, including apps for such, a dedicated hardware interface, or another appropriate user interface mechanism. The user input device may be a physical device or software application, including a keyboard, a touchscreen, voice commands, or wireless connections with a smart device (e.g., smartphone app or similar). As shown in FIG. 1, the sensor unit of the system transmits a radio wave signal and then receives the signal back in step 102 (i.e., radar). The received signals are transmitted to a control unit, where, in step 104, they are analyzed using logic programmed on the microcontroller or other processor. The received signals may also be stored in memory (e.g., flash memory). The microcontroller, in step 106, is configured to identify whether a signal received is static (i.e., non-moving) or dynamic/phase varying signal (e.g., heartbeat, lungs, skin displacement, etc.). This may be accomplished using a human-determining radar application (software that is programmed to extract and compare the dynamic signal to the dynamic signals stored in memory). While the foregoing radar description is not exhaustive, an exemplary radar system is disclosed in U.S. Patent Application US20140316261A1 titled, "Life Detecting Radars" to Lux et al., which is incorporated herein by reference in its entirety. Continuing, if no human signal is present (i.e., all radio wave signals received were static), then the structure is secure (step 108). If a signal is dynamic (i.e., consistent with that of an occupant (e.g., heartbeat and/or breathing detected)), then the signal is compared in step 110 to signals stored in memory. The signals in memory were recorded at installation of the system, according to the user's desires. If in steps 112 and 114, the signal is authorized (i.e., the received signal matches a signal in memory), then the house is secure. In steps 112 and 116, if, based upon the logic, a triggering event has occurred (i.e., the received signal does not match a signal in memory), an alert is activated. Triggering events may vary according to user desire and according to the number of sensor units deployed in the house. Example triggering events are as follows: the number of heartbeats in a home drops below, or exceeds, a predetermined threshold; an unrecognized heartbeat enters the home; a known heartbeat is in the home during unauthorized hours; a known heartbeat becomes irregular; and others. The alert may comprise an alert device that provides an alert to a user of the monitoring system, including: 1) a home alarm such as an audible speaker or visually detectable indicator or light; 2) a notification to an internet connected device (e.g., smartphone, tablet, vehicle, etc.); 3) contacting emergency responders or other third-parties; and others.

A significant improvement over the prior art is the ability to monitor the home constantly, without the need to "arm" or "disarm" the system. For example, the control unit may be programmed to recognize heartbeats of specific people. This may be accomplished during an initial configuration of the system. For example, each occupant's unique heartbeat and/or breathing pattern may be read and stored in memory of the system. For example, a particular sensor may be used for a calibration mode, wherein when a heartbeat is received by the control unit from the sensor in calibration mode, an option is made available to name the received signal and set a trust level. Various trust levels may be assigned by a user, allowing the user to distinguish between occupants who live there and visitors. For example, a user may not want an alert if a known neighbor enters the home during the day (neighbor child), but would wish to be alerted if the neighbor is entering at night. As such, when the control unit analyzes the received signal and compares it with signals stored in memory, it "recognizes" each individual.

In another embodiment, rather than pre-programming neighbors, friends, and others, a control unit may be programmed to recognize familiar heartbeats based upon the number of visits to the house, and, if the user desires, the alert may be deactivated. For example, if a neighbor frequently visits the home, the homeowner, rather than formally entering the neighbor into the system, may simply set the system to not activate an alert after the fourth separate entry of the occupant (or whatever number the homeowner desires). Also, it will be appreciated that the homeowner/user can select the type of alerting means to be activated. For example, a user may select a mobile alert (e.g., text message) vs. house alarm (e.g., audible alarm using speakers) vs. contacting emergency responders, etc., depending upon the triggering event. For example, an unknown heartbeat being detected in the middle of the night may warrant more aggressive alerting means (e.g., home loudspeaker) than during the late afternoon when friends are known to visit (e.g., text message). Again, the types of alerts are selectable by a user, along with the triggering events, using programmed computer software.

Figure 4:
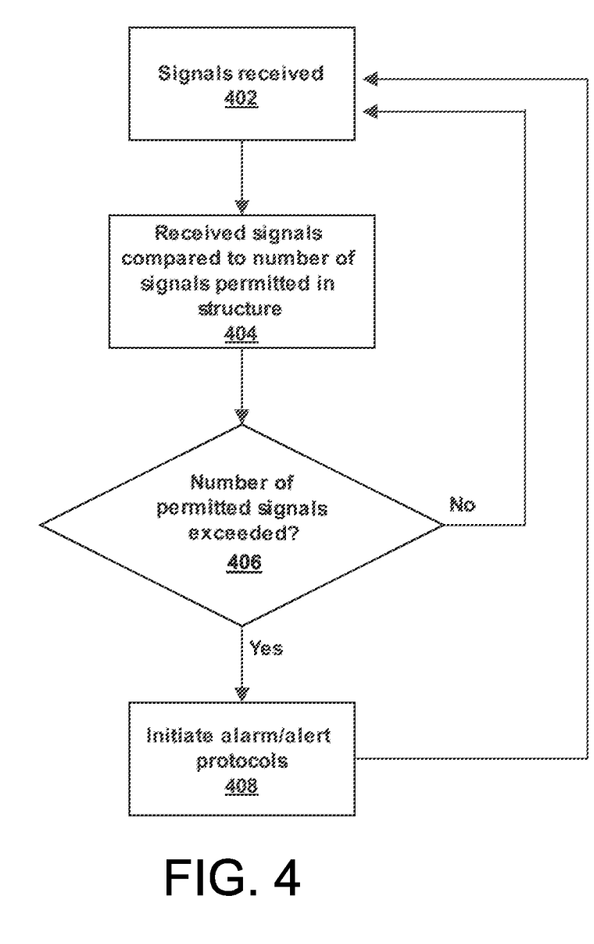
FIG. 4 is a flowchart of a home occupant detection and monitoring system.

In one embodiment, a method of detecting occupants in a structure comprises using radar (e.g., radio waves) to detect one or more occupants within a structure and compares the total number of occupants within the structure with the total number of occupants allowed in the structure, as programmed by a user. FIG. 4 illustrates a flowchart of this embodiment. As shown in step 402, radio wave signals are received by a sensor unit and are transmitted to a control unit, where, in step 404, the number of human signals (e.g., received signals that are indicative of human life, such as a heartbeat or breathing patterns, etc.) are compared against the total number of authorized individuals. In step 406, if the number of received signals do not exceed the number of allowed signals, the system loops. However, if the microcontroller concludes that the number of received signals exceeds the number authorized, an alert is initiated in step 408. For example, a user having a house with four occupants may configure the control unit to activate the alerting means if the number of heartbeats exceeds four within the structure. To prevent unwanted alerts, a user may choose a timeframe for notification (e.g., 10 pm to 7 am) or another parameter. Likewise, the system may be programmed to initiate an alert/alarm if the number of human signals received drops below a given number, which may be useful in detecting when, for example, teens are sneaking out, when a handicapped or otherwise impaired individual (e.g., Alzheimer's disease) wanders off, or other uses, as desired by a user. It will likewise be appreciated that the sensor unit may continuously transmit (e.g., continuous radio wave/FMCW) and receive signals, or may do so intermittently.

Further, the sensor unit(s) may be placed in one or more locations, depending upon the structure and the notifications desired by a user. For example, in one embodiment, a single sensor unit may be placed in the apex of an attic, where it may transmit radio wave signals downward throughout an entire house for the purpose of monitoring the entire house with a single sensor unit. However, such a system may have limitations in some configurations, such as health monitoring or undesired wandering off. For example, with a single sensor system, the control unit may not be able to adequately detect when an occupant has left the structure vs. suffered from cardiac arrest. Therefore, in another embodiment, a user may place additional sensors at thresholds so as to accurately identify who and when an occupant exits the home. For example, in a home having an Alzheimer's patient, it may be desirable to only sound an alarm when that patient exits a threshold, rather than sounding when anyone leaves. Further, there may be events when the control unit no longer detects a signal which was previously present, which has not exited through a threshold. In such a circumstance, it would be desirable to initiate an alert/alarm so that others in the house may check on the individual in case of a health problem (e.g., cardiac arrest, suffocation, etc.).

Figure 2:
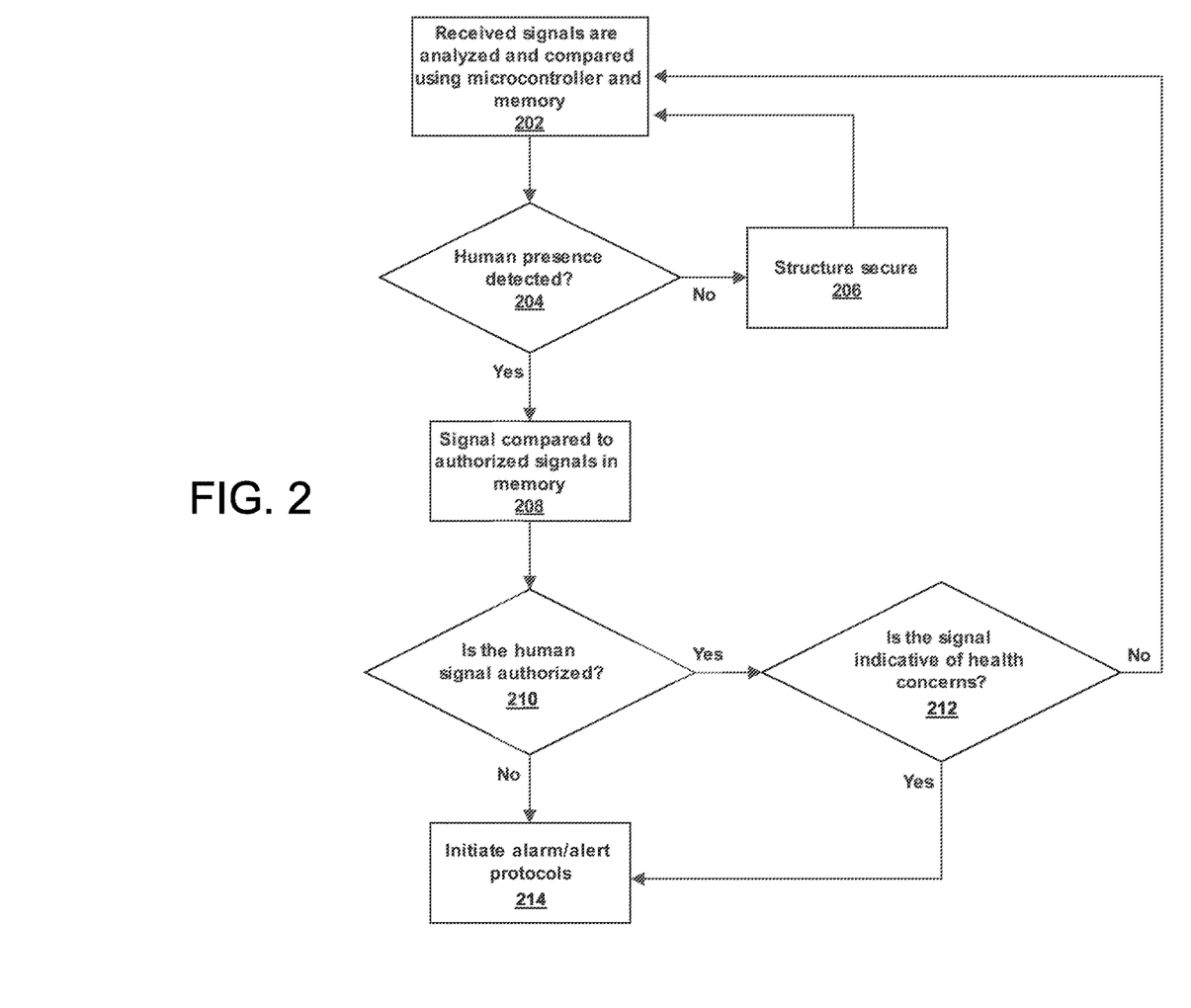
FIG. 2 is a flowchart of a home occupant detection and monitoring system.

FIG. 2 illustrates a flowchart wherein the system both verifies that the human is authorized to be in the home, and likewise compares the signal against known, previously inputted signals, to verify the health status of the individual. In step 212, signals indicative of health concerns (i.e., an irregular radar signal) may be when the heart rate is increased or decreased beyond a set of preprogrammed parameters (which may be known standards in healthcare or specific to an individual—which may be accomplished during calibration by taking several readings over the course of time and perhaps days, and including pre- and post-workout, etc.), when the respiration rate is outside of programmed parameters, and others.

In another embodiment, a plurality of sensor units (or separate transmitter and receivers) may be used and may be placed in individual rooms for more direct readings and for the purpose of more easily identifying the location of the heartbeat. The sensor units may also be concealed behind walls, ceilings, in fixtures (e.g., appliances, light bulbs) or personal items (e.g., picture frames). For example, each sensor unit may be uniquely identifiable (e.g., MAC address, IP address, etc.) such that the control unit is able to determine which sensor unit sent the signal to the control unit. In other words, a control unit may be programmed at installation/calibration when the sensor units are installed (e.g., sensor unit "Five" is located in the "living room"). In such a scenario, the alerting means may indicate to a user not only that an unknown heartbeat has entered the structure, but may also actively determine which room the stranger is located. Further, if the system is also configured to monitor health (as discussed elsewhere herein), the system may be able to identify the occupant and the location of the occupant having an emergency (e.g., respiratory distress in a child's room). Each sensor unit may be in direct communication with the control unit, or may be configured in a mesh network with signals being relayed to the control unit for analysis. Further, it will be appreciated that the sensor units may be omnidirectional, unidirectional, fixed, pivotable, etc. Further, the antenna of the sensor unit may be pivotable in relation to the sensor unit.

In one embodiment, a method of detecting occupants in a structure comprises using radar to detect one or more occupants within a structure, using programmed logic to compare the received radar signals with one or more stored signals, and identifying the occupants based upon the radar signals.

Figure 3:
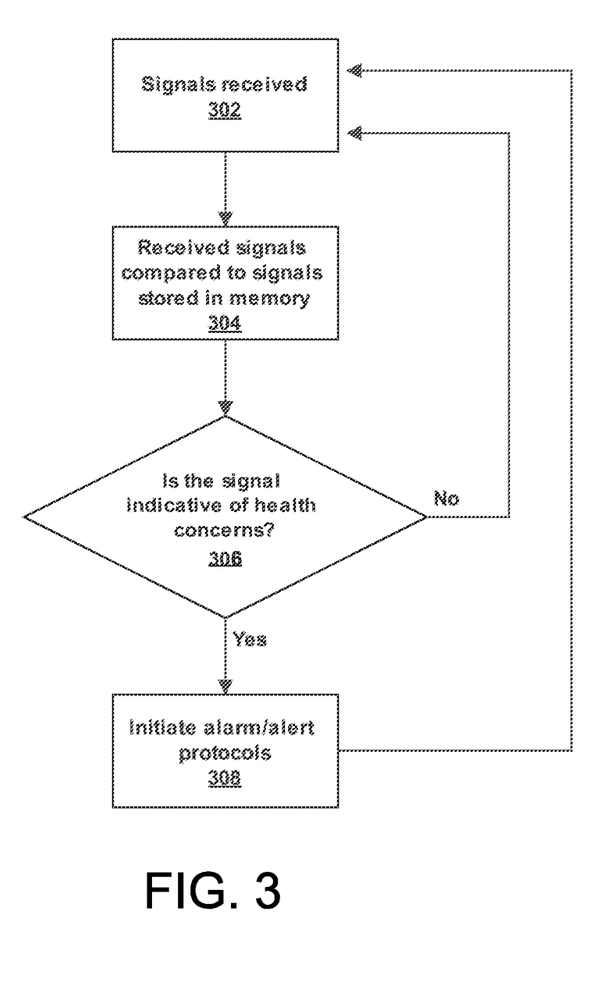
FIG. 3 is a flowchart of a home occupant detection and monitoring system.

In one embodiment, as shown in FIG. 3, the system may be used to only identify health concerns. In other words, it is not necessary for the system to be used as both security and health monitoring. A health monitoring system as shown in FIG. 3, may be well suited for care facilities, schools, or other situations where the need to monitor specific/special needs individuals is critical. In such a scenario, radar may be used to generate a signal of each individual that needs monitoring. The returned radar signal (i.e., the received signal) may then be stored in memory of the control unit. As the control unit then continues to receive signals, it compares those received signals with the signals in memory (step 306) to determine if the received signals are irregular radar signals (e.g., increased heart rate, increased respiration, etc.). If an irregular signal is received, an alert/alarm is initiated in step 308. Likewise, the system may be configured to monitor thresholds to help prevent unwanted wandering off of specific/special needs individuals, which may be particularly beneficial in schools and care facilities where it may be difficult for adults to maintain constant care of individuals.

In one embodiment, a method of detecting, identifying, and monitoring users comprises using radar to detect one or more occupants within a structure, using programmed logic to compare the radar signals with one or more stored signals, and identifying the occupants based upon the radar signals, wherein when an irregular radar signal is received from one or more known occupants, alerting one or more occupants to the irregular radar signal received. Again, the alerts may take the form of phone calls, text messages or emails, third-party contact, audible house alarms or verbal information via speakers, or contacting emergency responders.

In addition to the above uses of the technology, received signals (e.g., heartbeat and respiration patterns) may be recorded/stored for additional uses, such as by law enforcement in prosecuting an individual. For example, an invader's heartbeat data would be collected and stored by the control unit. The information may then be used to verify that the correct individual has been apprehended—like fingerprint or DNA evidence is currently used. Convenience stores or other establishments may place a sensor at the threshold for the purpose of cataloging individuals. If an individual were to attempt to rob the store, the data may be used in combination with video cameras and timestamps to identify the signal of the thief. If a repeat offender, the authorities could more quickly locate the individual—no disguise would shield the would-be thief from vital sign detection. Further, if a suspect is apprehended, the radar signals may be compared for confirmation.

In one embodiment, a home occupant detection and monitoring system comprises a radio wave transmitter capable of transmitting Frequency Modulated Continuous Wave (FMCW) signals; one or more radio wave receivers positioned in orthogonal locations (or, in general, non-parallel locations) around an environment to be monitored; a user interface comprising a microcontroller, a wireless transceiver, a means for user input, and a network card; and, a means for alerting occupants and third-parties to a triggering event; wherein the microcontroller, based upon logic, activates the alerting means at a triggering event. The FMCW allows for discrimination of multiple targets at distinct distances. Further, placing the receivers (or receiving antennas) at non-parallel locations, allows for the disambiguation of subjects that may be at the same distance from one of the receivers.

In one embodiment, a home occupant detection and monitoring system comprises a radio wave transmitter capable of transmitting FMCW, wherein the FMCW is configured to map walls of a structure by measuring distance of walls and objects with maximum return. By mapping a home, a user may be presented with the map and location of subjects on the map. For example, the map and subject location may be transmitted to a user's smartphone, allowing the user to identify locations of occupants in any given structure. In one, non-limiting example, a user may transmit a signal from a smartphone to a server or other network-connected device requesting the map. The map may then be transmitted to the user, wherein occupants are displayed on the map. In another example, an alert and the map are transmitted to a user at a triggering event (i.e., home should be vacant when away on vacation, and an occupant is detected). In one embodiment, cameras may coupled to the system such that a user may view the room/occupant in real-time.

In one embodiment, an antenna of the radio wave transmitter, receiver, or transceiver rotates, either electronically or mechanically, to monitor an environment using narrow beam scanning (e.g., +/−45 deg.). In an alternate embodiment, the antenna would use wide (e.g., 90 deg.) beam scanning with a moveable, higher gain antenna to scan the environment for vital signals. In other words, the higher gain antenna would continually sweep the room, detecting vital signs of occupants.

One example radar technology capable of detecting heartbeats is NASA's Finder technology. The Finder technology is a mobile system intended for locating live occupants in disaster scenarios. For example, if a building collapses as the result of an earthquake, the Finder system may be used to scan the rubble and detect any living individuals. The technology is disclosed in U.S. Patent Publication US20140316261A1 and is incorporated herein by reference in its entirety. While this system is very beneficial for that use, it is not capable of detecting occupants in a home and activating alerting means in response to triggering events.

Another technology, known as HERMA and disclosed in U.S. Patent Publication US20160048672A1, discloses the use of radio wave authentication and is also incorporated herein by reference in its entirety. That disclosure is aimed at user authentication, such as biometrics. While the above two references discuss similar technologies, which may be incorporated into the current invention, neither system discloses, or is capable of, detecting, identifying, and monitoring users in a home or other structure. As such, the present disclosure solves those problems.

Therefore, as appreciated from the above disclosure, the home occupant detection and monitoring system solves the problems in the prior art, namely, the ability to detect an occupant without the need of monitoring structural items (e.g., doors and windows), the ability to determine the number of occupants within a structure, their location, and their current health status.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention as defined in the appended claims. Additionally, it is not intended that the scope of patent protection afforded the present invention be defined by reading into any claim a limitation found herein that does not explicitly appear in the claim itself.

What is claimed is:

1. A method of detecting and monitoring occupants in a building comprising:
   using radar to detect human signals of multiple occupants within the building, wherein the step of using radar to detect the human signals comprises using a transmitter having an antenna to transmit a narrow beam radio frequency signal and receiving a return of the narrow beam radio frequency signal;
   rotating the antenna such that the narrow beam of the radio frequency sweeps one or more rooms of the building;
   comparing a number of occupants whose human signals were detected by the radar within the building to a number of occupants previously allocated by a user; and
   upon determining that the number of occupants detected is greater than the number of occupants allocated, alerting one or more individuals.

2. The method of claim 1, wherein the antenna is rotated mechanically.

3. The method of claim 1, wherein the antenna is rotated electronically.

4. The method of claim 1, wherein the one or more individuals are alerted via a mobile alert.

5. The method of claim 1, wherein the one or more individuals are alerted via a house alarm.

6. The method of claim 1, wherein the human signal comprises information with regard to a heartbeat of the occupant.

7. The method of claim 1, wherein the human signal comprises information with regard to a breathing pattern of the occupant.

8. A method of detecting and monitoring occupants in a building, comprising:
   producing a signal and transmitting the signal comprising radio waves from a transmitting antenna to one or more rooms of a building;
   receiving a returned signal in a receiving antenna, wherein the returned signal comprises information with regard to a returned human signal of an occupant of the one or more rooms;
   comparing the returned human signal information with information contained in or more stored signals comprising stored human signal information; and
   identifying the occupant based upon the comparison of the returned human signal information to the stored human signal information.

9. The method of claim 8, wherein upon determining that the returned human signal information does not correlate to the stored human signal information, activating an alert device.

10. The method of claim 8, further comprising the step of comparing the returned human signal information with the stored human signal information to determine if the returned human signal information comprises an irregular signal; and wherein when an irregular signal is received, alerting one or more occupants to the irregular signal received.

11. The method of claim 8, further comprising initiating an alert or alarm when an occupant leaves the structure.

12. The method of claim 8, wherein the human signal information comprises information regarding an occupant's heartbeat.

13. The method of claim 8, wherein the human signal information comprises information regarding an occupant's breathing pattern.

14. The method of claim 10, wherein the irregular signal comprises information indicating an increase in heart rate.

15. The method of claim 10, wherein the irregular radar signal comprises an information indicating an increase in respiration.

16. The method of claim 8, further comprising a step of storing stored human signal information for an occupant when the occupant visits the one or more rooms of a building a predetermined number of times.

17. The method of claim 12, wherein the stored human signal information comprises information indicative of an occupant's unique heartbeat.

18. The method of claim 13, wherein the stored human signal information comprises information indicative of an occupant's unique breathing pattern.

19. The method of claim 8, wherein the step of transmitting the signal comprises transmitting a Frequency Modulated Continuous Wave signal, and the step of receiving the returned signal comprises receiving a return of the Frequency Modulated Continuous Wave signal.

20. The method of claim 8, wherein the step of transmitting the signal comprises the step of transmitting a narrow beam radio frequency signal, and the step of receiving the returned signal comprises receiving a return of the narrow beam radio frequency signal.

\* \* \* \* \*